(12) United States Patent
Leeson et al.

(10) Patent No.: US 10,195,136 B2
(45) Date of Patent: Feb. 5, 2019

(54) COLLAGEN AND ELASTIN STIMULATING COMPOSITIONS AND USES THEREOF

(75) Inventors: Daniel Thorn Leeson, New York, NY (US); Uma Santhanam, Tenafly, NJ (US); John W. Lyga, Basking Ridge, NJ (US); Siming W. Chen, Basking Ridge, NJ (US); Russell Wyborski, Pine Island, NY (US)

(73) Assignee: AVON PRODUCTS, INC., Rye, NY (US)

( * ) Notice: Subject to any disclaimer, the term of this patent is extended or adjusted under 35 U.S.C. 154(b) by 79 days.

(21) Appl. No.: 13/216,626

(22) Filed: Aug. 24, 2011

(65) Prior Publication Data

US 2013/0052288 A1 Feb. 28, 2013

(51) Int. Cl.
| | |
|---|---|
| *A61K 8/97* | (2017.01) |
| *A61K 36/19* | (2006.01) |
| *A61K 36/48* | (2006.01) |
| *A61Q 19/08* | (2006.01) |

(52) U.S. Cl.
CPC ............. *A61K 8/97* (2013.01); *A61K 36/19* (2013.01); *A61K 36/48* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,146,640 A | 11/2000 | Dyke | |
| 7,101,663 B2 | 9/2006 | Godfrey et al. | |
| 7,662,561 B2 | 2/2010 | Godfrey et al. | |
| 8,128,914 B2 | 3/2012 | Ptchelintsev et al. | |
| 8,394,427 B2 | 3/2013 | Zheng et al. | |
| 8,512,764 B2 | 8/2013 | Paufique | |
| 8,771,758 B2 | 7/2014 | Ptchelintsev | |
| 8,802,167 B2 | 8/2014 | Hwang et al. | |
| 9,034,396 B2 | 5/2015 | Zheng et al. | |
| 9,066,896 B2 | 6/2015 | Zheng et al. | |
| 9,186,316 B2 | 11/2015 | Khusial et al. | |
| 9,238,000 B2 | 1/2016 | Khusial et al. | |
| 2003/0207818 A1 | 11/2003 | Jia et al. | |
| 2004/0156886 A1 | 8/2004 | Kose | |
| 2005/0147578 A1 | 7/2005 | Menon et al. | |
| 2006/0013782 A1 | 1/2006 | Mahalingam et al. | |
| 2006/0024390 A1 | 2/2006 | Schauss et al. | |
| 2006/0134059 A1 | 6/2006 | Dryer et al. | |
| 2006/0134231 A1 | 6/2006 | Hines et al. | |
| 2006/0193819 A1 | 8/2006 | Lu et al. | |
| 2007/0224272 A1 | 9/2007 | Touitou | |
| 2010/0158828 A1 | 6/2010 | Ptchelintsev et al. | |
| 2010/0267643 A1 | 10/2010 | Baron et al. | |
| 2011/0052737 A1 | 3/2011 | Florence et al. | |
| 2012/0003332 A1 | 1/2012 | Zheng et al. | |
| 2013/0053423 A1 | 2/2013 | Lyga | |
| 2013/0102606 A1 | 4/2013 | Hwang et al. | |
| 2013/0149268 A1 | 6/2013 | Chen et al. | |
| 2013/0149397 A1 | 6/2013 | Chen et al. | |
| 2014/0161910 A1 | 6/2014 | Zheng et al. | |
| 2014/0255523 A1 | 9/2014 | Ptchelintsev et al. | |

FOREIGN PATENT DOCUMENTS

| | | |
|---|---|---|
| CN | 1795888 A | 7/2006 |
| CN | 101099839 A | 1/2008 |
| CN | 101129675 A | 2/2008 |
| CN | 101234153 A | 8/2008 |
| EP | 1441686 B1 | 7/2008 |
| JP | 2000128730 A * | 5/2000 |
| JP | 2002087973 A | 3/2002 |
| JP | 2006069954 A | 3/2006 |
| JP | 4280340 B2 | 6/2009 |
| JP | 2010090069 A | 4/2010 |
| WO | 2000053156 | 9/2000 |
| WO | 2006068778 A2 | 6/2006 |
| WO | 2007093839 A1 | 8/2007 |
| WO | 2012005872 A1 | 1/2012 |

OTHER PUBLICATIONS

Partial Translation of JP 2000-128730 A.*
Varani et al., Reduced Fibroblast Interaction with Intact Collagen as a Mechanism for Depressed Collagen Synthesis in Photodamaged Skin; The Journal of Investigative Dermatology; Jun. 6, 2004, vol. 122, p. 1471-9.
Varani et al.; Decreased Collagen Production in Chronologically Aged Skin; American Journal of Pathology, vol. 168, No. 6, Jun. 2006; p. 1861-8.
Fisher et al., Looking Older Fibroblast Collapse and Therapeutic Implications; Arch Dermatol/vol. 144 (No. 5), May 2008, p. 666-72.
Dayan et al. Indigenous Forest Tree Species in Laguna Provice, DENR Recommends, 2007, Vo.l 15b, pp. 1-25.
Kittibamruangsook. Effects of volatile oils extracted from some plants [*Azadirachta indica, Ternstroemia japonica, Cymbopogon citratus, Citrus hystrix*] to the oriental fruit fly (*Dacus dorsalis* Hendel) [in Thailand], Kasetsart Univ., Bandkok, Thesis or Dissertation, 1980; Abstract.
Devi et al. Anti Viral Medicinal Plants—An Ethnobotanical Approach. Journal of Phytology, 2009, vol. 1(6); pp. 417-421.
Yang et al., "AP-1 Pathway-targeted inhibition of inflammatory responses in LPS-treated macrophages and EtOH/HCI-treated stomach by Archidendron clypearia methanol extract," Journal of Ethnopharmacology, vol. 146, pp. 637-644 (2013).
Choi, Eun-Mi et al., "Screening of Indonesian medicinal plants for inhibitor activity on nitric oxide production of RAW264.7 cells and antioxidant activity," Fitoterapia, vol. 76, pp. 194-203 (2005).
Fujimoto, Norihiro et al., "Expression of microfibril-associated glycoprotein-1 (MAGP-1) in human epidermal keratinocytes," Arch. Dermatol. Res. vol. 292, pp. 21-26 (2000).
Jothi, G. J. et al., "Glimpses of Tribal Botanical Knowledge of Tirunelveli Hills, Western Ghats, India," Ethnobotanical Leaflets, vol. 12, pp. 118-126 (2008).

(Continued)

*Primary Examiner* — Terry A McKelvey
*Assistant Examiner* — Catheryne Chen
(74) *Attorney, Agent, or Firm* — Brian P. McCloskey

(57) ABSTRACT

Methods and compositions for preventing, ameliorating, or reducing dermatological signs of aging are provided which employ a botanical extract of *Justicia ventricosa, Archidendron clypearia, Abrus fruticulosus*, or combinations thereof and a cosmetically acceptable vehicle.

14 Claims, No Drawings

(56) References Cited

OTHER PUBLICATIONS

Micor, Jose Rene L. et al., "Biological Activity of Bignay [*Antidesma bunius* (L.) Spreng] Crude Extract in Artemia salina," J. Med. Sci., vol. 5, No. 3, pp. 195-198 (2005).
Mintel, "Treatment Cream," Database GNPD [online], database accession No. 1646948 (2011).
Tatano, Yutaka et al., "Significant Decrease in Tropoelastin Gene Expression in fibroblasts from a Japanese Costello Syndrome Patient with Impaired Elastogenesis and Enhanced Proliferation," J. Biochem., vol. 140, pp. 193-200 (2000).
Kang, Sewon et al., "Topical N-Acetyl Cysteine and Genistein Prevent Ultraviolet-Light-Induced Signaling That Leads to Photoaging in Human Skin in vivo," The Society for Investigative Dermatology, Inc,; vol. 120, No. 5, pp. 835-841 (2003).
Nanasombat, S. et al., "Antimicrobial, antioxidant and anticancer activities of Thai local vegetables," Journal of Medicinal Plants Research, vol. 3, No. 5, pp. 443-449 (2009).
Singthong, Jittra et al., Extraction and physicochemical characterisation ofpolysaccharide gum from Yanang (*Tiliacora triandra*) leaves, Food Chemistry, vol. 114, pp. 1301-1307 (2009).
U.S. Appl. No. 13/710,617, filed Dec. 11, 2012, Zheng, Qian et al.
U.S. Appl. No. 13/602,557, filed Sep. 4, 2012, Zheng, Qian et al.
U.S. Appl. No. 12/648,581, filed Dec. 29, 2009, Lyga, John et al.
U.S. Appl. No. 13/305,779, filed Nov. 29, 2011, Zheng, Qian et al.
U.S. Appl. No. 14/284,869, filed May 22, 2014, Ptchelintsev, Dmitri.
U.S. Appl. No. 13/158,947, filed Jun. 13, 2011, Zheng, Qian et al.
U.S. Appl. No. 13/710,536, filed Dec. 11, 2012, Hwang, Cheng et al.
U.S. Appl. No. 14/066,862, filed Oct. 30, 2013, Lyga, John W. et al.
U.S. Appl. No. 14/055,037, filed Oct. 16, 2013, Khusial, Permanan Raaj.

\* cited by examiner

COLLAGEN AND ELASTIN STIMULATING COMPOSITIONS AND USES THEREOF

FIELD OF INVENTION

The present invention relates generally to methods and compositions for improving the aesthetic appearance and health of human skin. In particular, the invention relates to methods and compositions for increasing the production of collagen and elastin in the skin.

BACKGROUND

Consumers continually seek to improve the appearance of their skin and in particular to reduce visible signs of skin aging. Unwanted signs include lines and wrinkles, skin sagging or atrophy, loss of suppleness, thickness, plumpness, tautness, elasticity, resiliency, and firmness, and there remains a need for products that combat such signs of aging and, more generally, that provide anti-aging and/or anti-wrinkle effects.

Recent studies have revealed that dermal fibroblasts undergo morphology changes and cell body collapse in both chronically and photo-aged skin. See, e.g., Varani et al., 2004, J. Invest. Dermatol. 122:1471:9; and Varani et al., 2006, Am. J. Pathol. 168: 1861-8. Such alterations can lead to coarse, rough, and wrinkled appearance, which are characteristics of aged skin. Further studies suggest that collagen degradation along with altered integrin and focal adhesion molecules are factors contributing to the loss of a functional dermal collagen matrix, with the consequence of cell body collapse due to a loss of mechanical tension between fibroblasts and the matrix. See, e.g., Fisher et al., 2008, Arch. Dermatol. 144: 666-72.

It is therefore an object of the invention to provide new approaches for combating signs of skin aging. It is a further object of the invention to provide new compositions and methods to improve the overall appearance of skin, including treating, reversing, and/or preventing signs of aging, including signs of aging associated with degradation of the skins' collagen and/or elastin matrices, using effective amounts of compositions that stimulate the expression of mRNA encoding collagen and/or elastin.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, the present invention identifies new cosmetic benefits of the botanical extracts *Justicia ventricosa, Archidendron clypeuria,* and *Abrus ruticulosus.*

In one aspect, the invention provides methods for improving the aesthetic appearance of human skin comprising topically applying to an area of the skin in need thereof an effective amount of a botanical extract in a topically acceptable vehicle, wherein said botanical extract is selected from the group consisting of *Justicia ventricosa, Archidendron clypearia, Abrus fruticulosus,* and combinations thereof. The said extract is preferably present in an amount effective to up-regulate collagen and/or elastin mRNA expression in human skin fibroblasts. It is believed that up-regulators of collagen and/or elastin mRNA produced within human fibroblasts will lead to increased protein production within the cells, including the fibroblast specific proteins collagen and elastin. Given the importance of fibroblast-produced proteins to overall skin strength and health, upregulation of collagen and/or elastin mRNA is expected to have a beneficial effect on reducing the appearance of aging on skin.

In another aspect, the invention provides cosmetic compositions comprising a botanical extract of *Justicia ventricosa, Abrus fruticulosus,* or combinations thereof, with a topically acceptable vehicle.

In yet another aspect, cosmetic compositions are provided comprising a botanical extract of *Archidendron clypearia,* and a topically acceptable vehicle, in combination with one or more skin active agents selected from the group consisting of retinoids, anti-oxidants, α-hydroxy acids, glycolic acid, and thiodipropionic acid and esters thereof.

The compositions provided herein typically will be formulated in a cosmetically acceptable vehicle and topically applied to a human integument, such as the skin of the face, neck, hands, chest, legs, etc., hair, or nails, for a time sufficient to enhance the health or aesthetic appearance thereof.

Further aspects, features and advantages of the present invention will be better appreciated upon a reading of the detailed description of the invention.

DETAILED DESCRIPTION OF THE INVENTION

All terms used herein are intended to have their ordinary meaning unless otherwise provided. By "cosmetically acceptable" is meant that a particular component is generally regarding as safe and non-toxic at the levels employed. The term "prevent," as used herein, includes delaying the onset or progression of a particular sign of skin aging. The term "thin skin" includes skin that becomes thinner with chronological aging as well as prematurely thinned skin, which may be caused, for example, by photo-aging. The phrase "individual in need thereof" refers to a human that could benefit from improved dermal appearance or health, including males or females. The term "skin" includes, without limitation, the lips, skin of the face, hands, arms, neck, and chest. As used herein, the term "consisting essentially of" is intended to limit the invention to the specified materials or steps and those that do not materially affect the basic and novel characteristics of the claimed invention, as understood from a reading of this specification.

The botanical extracts are selected from the group consisting of *Justicia ventricosa, Archidendron clypearia, Abrus fruticulosus,* and combinations thereof, and may be used as active agents in cosmetic preparation and may be formulated with other cosmetically acceptable components, such as a vehicle, into a composition for topical application to the skin. The compositions are topically applied to the skin in effective amounts, by which is meant an amount sufficient to achieve a measurable improvement in skin health or reduction in one or more dermatological signs of aging. The improvements in the signs of skin aging may generally relate to improvement in the production of elastin and/or collagen, and include without limitation, the following:

(a) treatment, reduction, and/or prevention of fine lines or wrinkles,
(b) reduction of skin pore size,
(c) improvement in skin thickness, plumpness, and/or tautness;

(d) improvement in skin smoothness, suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) decreased by aging and/or menopause;
(n) improvement in skin moisturization;
(o) increase in skin elasticity and/or resiliency;
(p) treatment, reduction, and/or prevention of skin sagging;
(q) improvement in skin firmness;
(r) reduction of pigment spots and/or mottled skin
(s) improving the appearance of acne scars or marks;
(t) improving the appearance of stretch marks; and/or
(u) improvement in the appearance of cellulite.

In a preferred embodiment, the aesthetic improvement is treatment, reduction, and/or prevention of fine lines or wrinkles, in another embodiment of the invention, the said aesthetic improvement of said skin is improvement in thickness, plumpness, and/or tautness. In another preferred embodiment of the invention, the said aesthetic improvement of said skin is increase in skirt elasticity and/or resiliency. In another preferred embodiment of the invention, the said aesthetic improvement of said skin is treatment, reduction, and/or prevention of skin sagging. In another preferred embodiment of the invention, the said aesthetic improvement of said skin is improvement in skin firmness.

In practice, the compositions of the invention are applied to skin in need of treatment. That is, skin which suffers from a deficiency or loss in any of the foregoing attributes or which would otherwise benefit from improvement in any of the foregoing skin attributes. The skin is typically treated once or twice daily. The treatment may continue for a week, two weeks, four weeks, eight weeks, six months or longer.

In one embodiment the active agents are topically applied, in a cosmetically acceptable vehicle, to skin suffering from fine lines and/or wrinkles to prevent, treat, and/or amelioration the appearance of the fine lines and/or wrinkles in the skin, in this case, the compositions are applied to skin in need of treatment, by which is meant skin already having wrinkles and/or fine lines or skin that is at risk of developing fine lines and/or wrinkles. Preferably, the compositions are applied directly to the fine lines and/or wrinkles on the skin of the face, neck, chest, and/or hands.

In one embodiment, the invention is directed to a method of improving the aesthetic appearance of skin by increasing the production of collagen and/or elastin in the skin, the method comprising topically applying to an area of the skin in need thereof an effective amount of an agent that up-regulates collagen and/or elastin mRNA expression.

The term "agent" that up-regulates collagen and elastin mRNA encompasses botanical extracts of *Justicia ventricosa, Archidendron clypearia, Abrus fruticulosus*, and combinations thereof. These agents up-regulate the cellular levels of collagen and elastin mRNA, by which is meant that the cellular levels of collagen and elastin proteins are increased by the active agent. The term "up-regulate" refers to up-regulation, induction, stimulation, and/or potentiation. The active agents may be, without limitation, activators or agonists, which are compounds that, for example, bind to, stimulate, increase, open, activate, facilitate, enhance activation, sensitize, or up-regulate expression levels of genes or collagen or elastin proteins or peptides. The mechanism by which the collagen or elastin protein are increased is not important.

As used herein, the term "expression levels" refers to an amount of a gene and/or protein that is expressed in a cell. As used herein, a "gene" includes a polynucleotide containing at least one open reading frame that is capable of encoding a particular polypeptide. As used herein, the terms "polynucleotide" is synonymous with "oligonucleotide" and includes polymeric forms of nucleotides of any length, either deoxyribonucleotides or ribonucleotides, or analogs thereof, including, without limitation, mRNA, DNA, cDNA, primers, probes, and the like.

The preferred methods for measuring expression levels of mRNA encoding collagen and/or elastin involve the quantitation of mRNA expression. Suitable methods for determining mRNA expression include quantitative PCR (QPCR), real-time QPCR, reverse transcription PCR (RT-PCR), and quantitative reverse transcription PCR (QRT-PCR), as are well-known in the art. As described in detail in U.S. Pat. Nos. 7,101,663 and 7,662,561, the disclosures of which are hereby incorporated by reference, a quantitative reverse transcriptase polymerase chain reaction (QRT-PCR) for detecting mRNA may include the steps of: (a) incubating an RNA sample from the cellular lysate with a reverse transcriptase and a high concentration of a target sequence-specific reverse transcriptase primer under conditions suitable to generate cDNA; (b) subsequently adding suitable polymerase chain reaction (PCR) reagents to the reverse transcriptase reaction, including a high concentration of a PCR primer set specific to the cDNA and a thermostable DNA polymerase to the reverse transcriptase reaction; and (c) cycling the PCR reaction for a desired number of cycles and under suitable conditions to generate PCR products ("amplicons") specific to the cDNA. The products of the QRT-PCR process may be compared after a fixed number of PCR cycles to determine the relative quantity of the RNA species as compared to a given reporter gene, for example, by Southern blotting. More typically, the progress of the PCR reaction is monitored by analyzing the relative rates of amplicon production for each PCR primer set, for example, by (1) non-specific fluorescent dyes that intercalate with any double-stranded DNA, and/or (2) sequence-specific DNA probes consisting of oligonucleotides that are labeled with a fluorescent reporter which permits detection only after hybridization of the probe with its complementary DNA target.

The mRNA may be any mRNA that is associated with collagen and/or elastin proteins, including the mRNAs encoding the subunits identified in Table 1 (COL1A1 and ELN). In a preferred embodiment, the mRNA encodes human COL1A1 and ELN.

In one embodiment, the plant materials and botanical extracts which up-regulate collagen and elastin mRNA expression may be made of extracts from the following species *Justicia ventricosa, Archidendron clypearia, Abrus fruticulosus*, or combinations thereof.

*Justicia ventricosa* is a species of the acanthaceae family, native to China, Burma (Myanmar), India, and Pakistan. It has medium-sized leaves and it produces small white flowers with red spots, it has been used in traditional Chinese medicine, and it is believed to invigorate the circulation of blood, remove hemorrhage, congestion, thrombosis, and local ischemia (microclots) and tissue changes, alleviate lower back pain and pain in lower extremities, traumatic injury, sprain, and arthritis.

*Archidendron clypearia* is a small evergreen tree, in the fabaceoe family. It typically has small leaves and produces small while-yellow flowers and orange-red fruits coiled with black seeds. Its leaves have been used for tanning and coloring rattan. It is found in India, Burma (Myanmar), southern China, Malaysia, Thailand, Sri Lanka, Laos, and also in Borneo. It is also known as *Inga clypearia, Jack Pithecellobium subcoriaceum*, and in Tamil as Malaivagai, Mazhavagai. In Borneo it is called Anup-anup, Jerung, Kangkat rangkat, Kelayung, Petai kerayung, and Tambilit.

*Abrus fruticulosus* is a perennial climbing shrub in the fabaceoe family. It is a plant native to the Indian subcontinent. It has 5-16 pairs of leaflets, and white pea-shaped flowers.

The plant materials may be in any form including, but not limited to, the whole plant, a dried plant, a ground plant, or parts thereof, including but not limited to, seeds, needles, leaves, roots, bark, cones, stems, rhizomes, callus cells, protoplasts, flowers, and meristems, or components and/or constituents found in, or isolated from, the natural plant material, and/or portions of the plant, or any combinations thereof. In one embodiment, the natural plant material is in the form of an extract derived from the whole plant or from a select portion of the plant, such as the leaves of the plant. It is to be understood that "natural plant material" also includes an ingredient, component, constituent, or extract derived from the natural plant material. In another embodiment, the plant extract as used herein, also includes "synthetic" extracts, various combinations of known plant components and/or constituents that are combined to substantially mimic the composition and/or activity of a plant extract of natural origin. Such synthetic extracts are included in the term "plant extract." The synthetic extracts will have two or more, three or more, or four or more active ingredients in common with a plant. Most preferably, the synthetic extracts will have substantially the same number of active ingredients as a natural extract. The correspondence of the numerical incidence of active ingredients between the synthetic extracts and the plant or a natural extract may also be described in terms of "percent commonality." Preferably, the synthetic extract has about 50 percent or more commonality to the chemical composition of a plant or natural extract. In other words, the synthetic extract has about 50 percent or more of the active ingredients found in the plant or a natural extract. More preferably, the chemical composition of the synthetic extract has about 70 percent or more commonality to the chemical composition of a plant or a natural extract. Optimally, a synthetic extract has about 90 percent or more commonality to the chemical composition of a plant or a natural extract.

In another embodiment, the composition comprises from about 0.0001% to about 90% by weight of a botanical extract of *Archidendron clypearia*, and a topically acceptable vehicle, in combination with one or more skin active agents selected from the group consisting of retinoids, anti-oxidants, α-hydroxy acids, glycolic acid, and thiodipropionic acid and esters thereof.

For use in the compositions of this disclosure, the plant extract or components and/or active constituents are preferably derived directly from the plant. The components may be in a pure form, a semi-pure form, or unpurified form. In one embodiment, the components are in the form of an extract obtained by aqueous or organic solvent extraction. Non-limiting examples of organic solvents include acetic acid, diethyl ether, ethyl acetate, lower alcohols (e.g., methanol, ethanol, isopropanol, butanol), dichloromethane, chloroform, hexane, benzene, toluene, xylene, petroleum ether, and combinations thereof. The solvent may be either polar or non-polar, protic or aprotic, water-miscible or water-immiscible. The pH may be acidic, neutral, or alkaline, Well-known methods in the art may be used for aqueous or organic solvent extraction. An extraction time between about 1-8 hours at a temperature between about 30° C. to about 90° C. is typically suitable. The collected extract is then fine-filtered to remove debris, and may be used directly, or is concentrated, for example by distilling the solvent or by other conventional processing, and the extract can also be provided in powder form.

The cosmetic compositions according to the invention can be formulated in a variety of forms for topical application and will comprise from about 0.0001% to about 90% by weight of the botanical extract, and preferably will comprise such actives in an amount from about 0.001% to about 25% by weight, and more preferably from about 0.01% to about 1%, 5%, or about 10% by weight. Combinations of botanical extracts are also contemplated. In another embodiment, the composition comprises a combination of two or more substances.

The compositions can include a cosmetically acceptable vehicle. Such vehicles may take the form of any known in the art suitable for application to skin and may include, but are not limited to, water; vegetable oils; mineral oils; esters such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and biphenyl alcohol; isoparaffins such as isooctane, isododecane and is hexadecane; silicone oils such as cyclomethicone, hydrocarbon oils such as mineral oil, petrolatum, isoeicosane and polyisobutene; polyols such as propylene glycol, glycerin, butylene glycol, pentylene glycol and hexylene glycol; liposomes; waxes; or any combinations or mixtures of the foregoing.

The vehicle may comprise an aqueous phase, an oil phase, an alcohol, a silicone phase or mixtures thereof and may be in the form of an emulsion. Non-limiting examples of suitable emulsions include water-in-oil emulsions, oil-in-water emulsions, silicone-in-water emulsions, water-in-silicone emulsions, glycerin-in-oil emulsions, wax-in-water emulsions, water-oil-water triple emulsions or the like. The emulsion may include an emulsifier, such as a nonionic, anionic or amphoteric surfactant, or a gelling agent.

The topical composition will typically have a pH range from 1 to 8, with a pH in the range of from 2 to 7 being preferred. In some embodiment, the composition will have a pH in the range of from 3.5 to 5.5. Suitable pH adjusters such as citric acid and triethanolamine may be added to bring the pH within the desired range.

In one embodiment of the invention, the compositions may include additional skin actives, including but not limited to, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors.

The composition may comprise additional active ingredients having anti-aging benefits, as it is contemplated that synergistic improvements may be obtained with such combinations. Exemplary anti-aging components include botanicals. Suitable botanical extracts include, without limitation, extracts from Abies pindrow, Acacia catechu, Anogeissus Asmunda japonica, Azadirachta indica, Butea frondosa, Butea monosperma, Cedrus deodara, Emblica officinatis, benghalensis, Glycyrrhiza glabra, Ilex purpurea Hassk, Innula racemosa, Ligusticum chiangxiong, Ligusticum lucidum, Mallottis philippinensis, Mimusops elengi, Morinda citrifolia, Moring oleifera, Naringi crenulata, Nerium indicum, Psoralea corylifolia, StenoIonia chusana, Terminalia belierica, tomato glycolipid, Sapindus rarak, Humulus japonicus, Eclipta prostrate, Amorphophallus campanulatus, Sesbania grandiflora, Pouzolzia pentandra, Melicope hayesii, Ixora chinensis, Erythina indica, Medemia noblis, Tiliacora triandra, Derris scandens, Portulaca oleracea, Alisma orientale, and mixtures thereof, Exemplary anti-aging compounds include, without limitation, phytol,thiodipropionic acid (TDPA) and esters thereof, retinoids (e.g., retinol and esters thereof, such as retinol palmitate, retinol acetate and retinol propionate, and salts thereof, all-trans retinoic acid, 9-cis retinoic acid, phytanic acid and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few. Further additional actives useful for topical application to skin include perilla oil, mangostine, palmitoyl lysylaminovaleroyl lysine (palmitoyl K-ava-K), palmatoyl tetrapeptide-10 (KTFK), L-4-thiazolylalanine, cis-6-nonenol, desthiobiotin, N-(4-mesyloxybenzyl)-N-methoxyethyl-4-chlorobenzene carboxamide. N-(4-mesyloxybenzyl)-N-isobutyl benzenesulfonamide, retinyl oleate, carvacrol, and mixtures thereof.

In another embodiment, the topical compositions of the present invention may also include one or more of the following: a skin penetration enhancer, an emollient, such as isopropyl myristate, petrolatum, silicones methicone, dimethicone), oils, mineral oils, and fatty acid esters; a humectant, such as glycerin or caprylyl glycol, a skin plumper, such as palmitoyl oligopeptide, collagen, or collagen and/or glycosaminoglycan (GAG) enhancing agents, a sunscreen, such as avobenzone, an exfoliating agent, and an antioxidant.

Suitable exfoliating agents include, for example, alpha-hydroxyacids, beta-hydroxyacids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. A preferred exfoliating agent is glycolic acid. When present, the exfoliating agent may comprise from about 0.1 wt % to about 80 wt of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Compositions of the present invention may comprise an antioxidant preferably from about 0.001 wt % to about 10 wt %, and more preferably from about 0.01 wt % to about 5 wt %, of the total weight of the composition.

Other conventional additives include: vitamins, such as tocopherol and ascorbic acid; vitamin derivatives such as ascorbyl monopalmitate; thickeners such as hydroxyalkyl cellulose; gelling agents; structuring agents, metal chelating agents such as EDTA; pigments; colorants, and pH adjusters. The composition may optionally comprise other components known to those skilled in the art including, but not limited to, film formers, moisturizers, minerals, viscosity and/or rheology modifiers, anti-acne agents, insect repellents, skin cooling compounds, skin protectants, lubricants, fragrances, skin conditioners, hair conditioners, lakes, dyes, preservatives, or stabilizers, and mixtures thereof. In addition to the foregoing, the cosmetic compositions of the invention may contain any other compound for the treatment of skin disorders.

The composition may be formulated in a variety of product forms, such as, for example, an emulsion, lotion, cream, serum, spray, aerosol, cake, ointment, essence, gel, paste, patch, pencil, towelette, mask, stick, foam, elixir, concentrate, and the like, particularly for topical administration. Preferably the composition is formulated as cream, an ointment, a gel, a serum, an emulsion, a spray, an aerosol, a patch, a mask, or a stick.

The invention provides a method for treating aging skin by topically applying a composition comprising a botanical extract, preferably in a cosmetically acceptable vehicle, over the affected area for a period of time sufficient to reduce, ameliorate, reverse or prevent dermatological signs of aging.

Generally, the improvement in the condition and/or aesthetic appearance is associated with the increase in collagen, procollagen, and elastin productions. Specific improvements are selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation or hypopigmentation; minimizing skin discoloration; improving skin tone, radiance, clarity and/or tautness; preventing, reducing, and/or ameliorating skin sagging; improving skin firmness, plumpness, suppleness and/or softness; improving (procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism decreased by aging and/or menopause; retarding cellular aging; improving skin moisturization; enhancing skin thickness; slowing or halting skin thinning; increasing skin elasticity and/or resiliency; enhancing exfoliation; improving microcirculation; decreasing and/or preventing cellulite formation; and any combinations thereof.

The composition will typically be applied to the skin one, two, or three times daily for as long as is necessary to achieve desired results. The treatment regiment may comprise daily application for at least one week, at least two weeks, at least four weeks, at least eight weeks, or at least twelve weeks or more. Chronic treatment regimens are also contemplated. The effect of a composition on the formation or appearance of fine lines and wrinkles can be evaluated qualitatively, by visual inspection, or quantitatively, by microscopic or computer assisted measurements of wrinkle morphology (e.g., the number, depth, length, area, volume and/or width of wrinkles per unit area of skin). In one embodiment, the composition of the invention will be applied to the skin in an amount from about 0.001 to about 100 mg/cm$^2$, more typically from about 0.01 to about 20 mg/cm$^2$, and preferably about 0.1 to about 10 mg/cm$^2$.

it is also contemplated that the compositions of the invention will be useful for treating thin skin by topically applying the composition to thin skin of an individual in need thereof "Thin skin" is intended to include skin that is thinned due to chronological aging, menopause, or photodamage and skin that is thinning prematurely. In some embodiments, the treatment is for thin skin in men, whereas other embodiments treat thin skin in women, pre-menopausal or post-menopausal, as it is believed that skin thins differently with age in men and women, and in particular in women at different stages of life.

The method of the invention may be employed prophylactically to forestall aging including in individuals that have not manifested signs of skin aging, most commonly in individuals under 25 years of age. The method may also reverse or treat signs of aging once manifested as is common in individuals over 25 years of age, or to slow the progression of dermatological aging in such individuals.

EXAMPLES

The following examples describe specific aspects of the invention to illustrate the invention but should not be construed as limiting the invention, as the examples merely provide specific methodology useful in the understanding and practice of the invention and its various aspects. In each case, the botanical extract was prepared from water/ethanol extraction of the indicated plant species.

Example 1

Extraction Procedure

An *Abrus fruticulosus* extract was prepared as follows. A sample of 250 g of dried material from the aerial portion of the plant was extracted with three portions of 1:1 ethanol/water (1335 ml, 800 ml, 700 ml) for a combined total of 2850 ml of extract. The ethanol was removed under vacuum, then sufficient additional water was added to achieve 1000 ml total volume. The resulting mixture was centrifuged at 8000 rpm for 10 minutes, then the supernatant was washed with three portions of dichloromethane (500 ml, 400 ml, 400 ml). The water phase was treated with 10 g of charcoal, filtered and then concentrated under vacuum to obtain 36.5 g of a solids. The same procedure was used to prepare the other extracts employed in Example 2.

Example 2

Elastin and Collagen Modulation Assay

Normal human dermal fibroblasts were cultured in 96-well tissue culture-treated plates, containing appropriate culture medium. Stock solutions of actives were made in an appropriate vehicle (water). Cells were treated with test material or respective vehicle control diluted in growth medium for 24 hours in a humidified 37° C. incubator with 10% $CO_2$. After incubation, growth medium from each plate was removed and 100 pt of lysis buffer was added to the wells and placed in 37° C. incubator with 10% $CO_2$ for 30 minutes. At the end of incubation, the cells were collected in freezer plates and placed in −80° C. freezer, until analysis, Changes in mRNA for Elastin (ELN) and Collagen (COL1A1) after treatment were analyzed using Panomics Quantigene multiplex assay that employs a branched DNA technology, following manufacturer's instructions (Affymetrix, CA). Percent increase in mRNA for Elastin (ELN) and Collagen (COL1A1) was calculated by comparing the test results to the control. The percent up-regulation or down-regulation is converted to a scaled score as shown below in Table 1

TABLE 1

| % Up-regulation | Up-regulation Scale |
| --- | --- |
| 0-20 | 0 |
| 21-40 | + |
| 41-60 | ++ |
| 61-80 | +++ |
| >81 | ++++ |

Up-regulation of Elastin or Collagen by Plant Extracts

A variety of botanical extracts were tested for their ability to up-regulate Elastin (ELN) and Collagen (COL1A1) according to the method of Example 1. The results are provided below in Table 2. The concentrations of each extract are provided based on the dry weight of the given plant extract, by which is meant the weight of the extract after volatile extraction solvents have been removed.

TABLE 2

| Ingredient Name | Elastin (ELN) Degree of upregulation (concentration of extract) | Collagen (COL1A1) Degree of upregulation (concentration of extract) |
| --- | --- | --- |
| *Abrus fruticulosus* | ++++ (0.1%) | 0 (0.1, 0.01%) |
| *Justicia ventricosa* | +++ (0.1%) | 0 (0.1, 0.01%) |
| *Archidendron clypearia* | ++ (0.1%) | ++ (0.1%) |

Example 3

Illustrative Compositions

The cosmetic compositions set forth in Table 3 are illustrative of the invention and are useful for topical application to the skin to enhance its aesthetic appearance.

TABLE 3

| Components | Composition: 1 Weight % | 2 | 3 | 4 | 5 |
|---|---|---|---|---|---|
| *Abrus fruticulosus* extract | 0.01 | 0.1 | — | — | — |
| *Justicia ventricosa* extract | — | — | 0.05 | — | — |
| *Archidendron clypearia* extract | — | — | — | 0.05 | 0.1 |
| Acrylates/C10-30 Alkyl Acrylate Crosspolymer | 1 | 1 | 1 | 1 | 1 |
| Cetyl Ethylhexanoate | 10 | 10 | 10 | 10 | 10 |
| C12-15 Alkyl Benzoate | 3.9 | 3.9 | 3.9 | 3.9 | 3.9 |
| Isopropyl Isostearate | 3 | 3 | 3 | 3 | 3 |
| Diisopropyl dimer dillinoleate | 0.1 | 0.1 | 0.1 | 0.1 | 0.1 |
| Tocopheryl acetate | 0.5 | 0.5 | 0.5 | 0.5 | 0.5 |
| Butylene glycol | 2 | 2 | 2 | 2 | 2 |
| Propylene glycol | 1 | 1 | 1 | 1 | 1 |
| Dimethicone PEG-7 isostearate | 0.5 | 0.5 | 0.5 | 0.5 | 0.5 |
| Methyl gluceth-20 | 0.5 | 0.5 | 0.5 | 0.5 | 0.5 |
| Triethanolamine | 1 | 1 | 1 | 1 | 1 |
| Acrylates/acrylamide copolymer/mineral oil | 1.5 | 1.5 | 1.5 | 1.5 | 1.5 |
| DMDM Hydantoin/ Iodopropynylbutylcarbonate | 0.4 | 0.4 | 0.4 | 0.4 | 0.4 |
| Deionized water | q.s. | q.s. | q.s. | q.s. | q.s. |
| Total: | 100 | 100 | 100 | 100 | 100 |

All percentages herein are indicated as percent by weight of the total composition (including vehicle) unless otherwise noted.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method for reducing appearance of one or more signs of aging in human skin comprising topically applying to an area of the skin in need thereof a composition comprising from about 0.01% to about 10% by weight of a botanical extract, in a topically acceptable vehicle in the form of an emulsion comprising an aqueous phase, and oil phase, and an emulsifier, wherein said botanical extract is an extract of a plant selected from the group consisting of *Justicia ventricosa, Archidendron clypearia*, and combinations thereof.

2. The method according to claim 1, wherein said reduction in one or more signs of said skin is selected from the group consisting of:
   (a) treatment and/or reduction of fine lines or wrinkles,
   (b) reduction of skin pore size,
   (c) improvement in skin thickness, plumpness, and/or tautness;
   (d) improvement in skin smoothness, suppleness and/or softness;
   (e) improvement in skin tone, radiance, and/or clarity;
   (f) improvement in procollagen and/or collagen production;
   (g) improvement in maintenance and remodeling of elastin;
   (h) improvement in skin texture and/or promotion of retexturization;
   (i) improvement in skin barrier repair and/or function;
   (j) improvement in appearance of skin contours;
   (k) restoration of skin luster and/or brightness;
   (l) replenishment of essential nutrients and/or constituents in the skin;
   (m) decreased by aging and/or menopause;
   (n) improvement in skin moisturization;
   (o) increase in skin elasticity and/or resiliency;
   (p) treatment, reduction, and/or prevention of skin sagging;
   (q) improvement in skin firmness;
   (r) reduction of pigment spots and/or mottled skin;
   (s) improving the appearance of acne scars or marks;
   (t) improving the appearance of stretch marks; and/or
   (u) improvement in the appearance of cellulite.

3. The method according to claim 2, wherein said reducing appearance of one or more signs of aging of said skin comprises reduction of fine lines and/or wrinkles.

4. The method according to claim 2, wherein thickness, plumpness, and/or tautness of said skin is improved.

5. The method according to claim 2, wherein skin elasticity and/or resiliency is increased.

6. The method according to claim 2, wherein said reducing appearance of one or more signs of aging comprises reduction of skin sagging.

7. The method according to claim 2, wherein skin firmness is improved.

8. The method according to claim 1, wherein the botanical extract is *Justicia ventricosa*.

9. The method according to claim 1, wherein the botanical extract is *Archidendron clypearia*.

10. The method according to claim 1, wherein collagen or procollagen production in the skin is increased.

11. The method according to claim 1, wherein elastin production in the skin is increased.

12. The method according to claim 1, wherein said extract is in an amount effective to up-regulate collagen and elastin mRNA expression in a human fibroblast.

13. A method for reducing the appearance of fine lines and/or wrinkles on skin of the face caused by aging comprising topically applying to said fine lines and/or wrinkles a water or water/ethanol extract of *Justicia ventricosa* that stimulates collagen production in the skin, in a topically acceptable vehicle in the form of an emulsion comprising an aqueous phase, and oil phase, and an emulsifier, for a period of time sufficient to reduce the appearance of said fine lines and/or wrinkles.

14. A method for reducing the appearance of fine lines and/or wrinkles on skin of the face caused by aging comprising topically applying to said fine lines and/or wrinkles a water or water/ethanol extract of *Archidendron clypearia* that stimulates collagen production in the skin, in a topically acceptable vehicle in the form of an emulsion comprising an aqueous phase, and oil phase, and an emulsifier, for a period of time sufficient to reduce the appearance of said fine lines and/or wrinkles.

* * * * *